United States Patent [19]

Engel et al.

[11] 3,974,282

[45] Aug. 10, 1976

[54] HYPOGLYCEMIC STILBAZOLTE DERIVATIVES

[75] Inventors: Kurt Engel, Basel, Switzerland; David Edward Thorne, Cranleigh, England

[73] Assignee: Beecham Group Limited, Great Britain

[22] Filed: May 12, 1975

[21] Appl. No.: 576,376

Related U.S. Application Data

[63] Continuation of Ser. No. 412,098, Nov. 2, 1973, abandoned.

[30] Foreign Application Priority Data

Nov. 4, 1972 United Kingdom............... 50924/72

[52] U.S. Cl............................. 424/263; 260/240 D; 260/240.9

[51] Int. Cl.$^2$................. A61K 31/44; C07D 213/06
[58] Field of Search.................. 424/263; 260/240 D

[56] References Cited
UNITED STATES PATENTS 2,558,777   7/1951   Papa et al. .......................... 260/289

OTHER PUBLICATIONS

Chemical Abstracts 61: 5606g (1964).

*Primary Examiner*—Leonard Schenkman

[57] ABSTRACT

Stilbazole derivatives in which the phenyl ring is substituted with a carboxylic acid group at the para position or a group convertible in the body to a carboxylic acid group, are useful as hypoglycemic agents.

3 Claims, No Drawings

HYPOGLYCEMIC STILBAZOLTE DERIVATIVES

This is a continuation of Ser. No. 412,098, filed Nov. 2, 1973, now abandoned.

This invention relates to a class of compounds which have hypoglycemic activity, to a method for their preparation and to pharmaceutical compositions comprising them.

During the course of our investigations into the hypoglycaemic activity of a large number of compounds we have noted a class of stilbazoles representative members of which have shown hypoglycemic activity in mice. On the basis of preliminary tests it appears that such activity is exhibited to a greater or lesser extent by the class as a whole. According to the present invention there is provided a class of compounds having formula (I) or formula (II) and acid addition salts thereof:

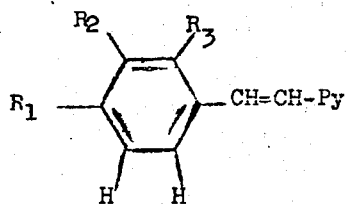

(I)

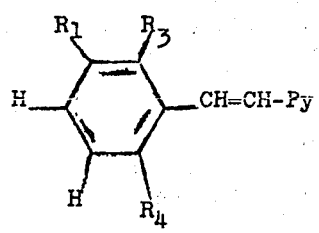

(II)

in which formulae the "Py" represents a substituted or unsubstituted 2-, 3-, or 4-pyridyl N-oxidised or quaternised pyridyl group: $R_1$ represents a carboxylic acid group, a group which is converted in the human body to a carboxylic acid group or an acyl group; $R_2$, $R_3$ and $R_4$ each separately represent hydrogen a carboxylic acid group, a group which is converted in the human body to a carboxylic acid group an acyl group a hydroxy group an alkoxy group, an aralkoxy or aryloxy group an esterified hydroxy group or a nitro halogen or amino group.

In the above definition of the compounds of this invention the symbol "Py" has been defined as a substituted or unsubstituted -2-. 3- or 4- pyridyl, N-oxidised or quaternised pyridal group. Preferably Py represents a 2- or 3-pyridyl group. The substituents which may be present include such common substituents as lower alkyl hydroxy, alkoxy aryloxy, aralkoxy halogen acyl amino nitro, carboxylic acid or carboxylic acid salt ester or amide derivatives. Preferably any substituents which are present in the pyridyl ring should be substituents which are converted in the human body to carboxylic acid groups. An example of a suitable substituted pyridyl group is a 6-methylpyrid-3-yl group.

Also in the definition of the compounds of this invention the symbols $R_1$ $R_2$ $R_3$ and $R_4$ may be inter alia groups which are converted in the human body to carboxylic acid groups. Examples of such groups include salt ester, or amide derivatives of carboxylic acid groups acyl group, substituted phenyl groups lower alkyl groups lower alkyl, alkenyl or alkynyl groups (especially those having an odd number of carbon atoms). lower alkyl alkenyl or alkynyl groups which carry substituents such as hydroxy alkoxy aryloxy aralkoxy esterified hydroxy or carboxylic substituents or a salt ester or amide derivative of a carboxylic acid substituent.

The stereochemical configuration about the double bond in compounds of formula (I) or (II) may be either cis or trans.

A preferred sub-group of compounds according to the invention consists of compounds of formula (IV) and acid addition salts thereof:

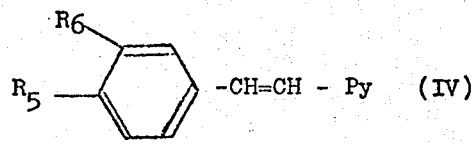

wherein Py represents a 2-, 3-, or 4-pyridyl group which is unsubstituted or is substituted in the meta-or-para-position (relative to the Py — CH bond) by a carboxylic acid group or a salt, ester or amide derivatives of a carboxylic acid group or an alkyl group having an odd number of carbon atoms or an alkyl group having an even number of carbon atoms carrying a carboxylic acid substituent or a salt, ester or amide substituent; and $R_5$ and $R_6$ separately represent hydrogen or carboxylic acid groups or salt, ester or amide derivatives of carboxylic acid groups or alkyl groups having an odd number of carbon atoms or alkyl groups having an even number of carbon atoms and carrying carboxylic acid substituents or salt, ester or amide substituents or a hydroxyalkyl or arylcarbonyl group at least one of $R_5$ and $R_6$ not being hydrogen.

Another preferred sub-group of compounds according to the invention consists of compounds of formula (V) and said addition salts thereof:

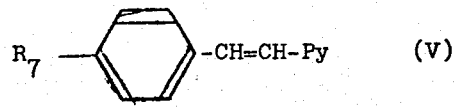

wherein Py represents an unsubstituted 2- 3- or 4-,pyridyl group and $R_7$ repesents a carboxylic acid or ester group or a $C_{1-7}$ alkyl group. Within this sub-class of compounds when the group $R_7$ is an ester group suitable ester groups are alkyl esters particularly a $C_{1-6}$ alkyl ester. Also it is preferable, when $R_7$ is a $C_{1-7}$ alkyl group that the alkyl group has an odd number of carbon atoms.

Examples of compounds falling within the scope of the present invention which are particularly preferred for their high level of hypoglycemic activity are the following and their pharmaceutically acceptable salts:

2-(4methylstyryl)-pyridine;
3-(4-methylstyryl)-pyridine;
4-(4-methylstyryl)-pyridine;
2-(4-carboxystyryl)-pyridine;
3-(4-carboxystyryl)-pyridine;
4-(4-carboxystyryl)-pyridine;
2-(4-methoxycarbonylstyryl)-pyridine;
3-(4-methoxycarbonylstyryl)-pyridine;
4-(4-methoxycarbonylstyryl)-pyridine;
2-(4-ethoxycarbonylstyryl)-pyridine;
3-(4-ethoxycarbonylstyryl)-pyridine;
4(4-ethoxycarbonylstyryl)-pyridine;

The acids which can be used to prepare acid addition salts of the compounds of this invention are suitably those which produce, when combined with the free base, salts whose anions are pharmaceutically acceptable. Examples of such acid addition salts are those derived from inorganic acids such as hydrochloric, hydrobromic nitro phosphoric and sulphuric acids and from organic acids such as acetic citric malic tartaric and lactic acids. When used in the form of its salt the stilbazole itself is the active portion of the molecule which produces the therapeutic effect but by suitable choice of salt the solubility absorbtion or other properties of the compound may be varied.

A particularly preferred compound of this invention is 2-(4-ethoxycarbonylstyryl)-pyridine of formula:

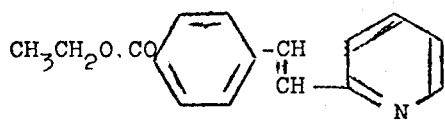

and its acid addition salts but high levels of hypoglycemic activity have been noted for other members of the present series as will become apparent from the Examples later in this specification. 2-(4-Ethoxycarbonylstyryl) pyridine is characterised by the following N.M.R. and IR data:- I.R. (KBr) Vmax 1695, 1105, 785 cm$^{-1}$ NMR (in CDCl$_3$):1.37 (d. J=4HZ. 1H aromatic proton); 1.8 – 3.0 (m.9H aromatic protons); 5.62 (q. J=HZ. 2H - OCH$_2$CH$_3$): 8.60 (t J=8HZ. 3H - OCH$_2$CH$_3$).

Compounds of the present invention may be prepared by a process which comprises reacting a compound of formula (IA), (IA'), (IIA) or (IIA') with a compound of formula (III) or reacting a compound of formula (IB) or (IIB) with a compound of formula (IIIA) or (IIIA'):

in which formulae (IA), (IA'), (IIA), (IIA') (IB) (IIB), (III) (IIIA) &(IIIA') the symbols R$_1$R$_2$R$_3$ R$_4$ and Py are as defined with respect to formulae (I) and (II) and R$_a$, R$_b$& R$_c$ are the same or different and each is lower alkyl, aryl or aralkyl.

It should be noted that on occasions it may be rather difficult to prepare compounds of formula (IIIA), since these compounds and their precursors are somewhat unstable. For this reason the preferred process for preparing the compounds of this invention comprises reacting compound (IA) or (IIA) with compound (III).

The reaction is usually carried out in an inert solvent such as dimethylformamide at a temperature of from about 10° to about 100°C. Under these conditions the reaction proceeds smoothly over a period of from a few minutes to a few hours and the product may be isolated by any of the usual techniques e.g. solvent evaporation or anti-solvent precipitation followed by filtration. In many cases the reaction may be carried out in a solvent in which the product is insoluble and in such cases the precipitated solid may be collected by filtration. Purification of the product may be by any of the usual chromatographic or recrystallization techniques.

During the preparation of the starting materials (IA), (IIA) (III) (IB) (IIB), or (IIIA), and indeed the end products (I) and (II) it may be desirable to protect any particularly reactive groups present. Thus, free carboxylic acid groups are preferably protected by esterification; free amino groups may be protected using the groups known for the purpose of peptide synthesis.

The preferred sub-class of compounds of this invention may be prepared by a number of alternate processes. The first such process relates to the preparation of a compound of formula (VI):

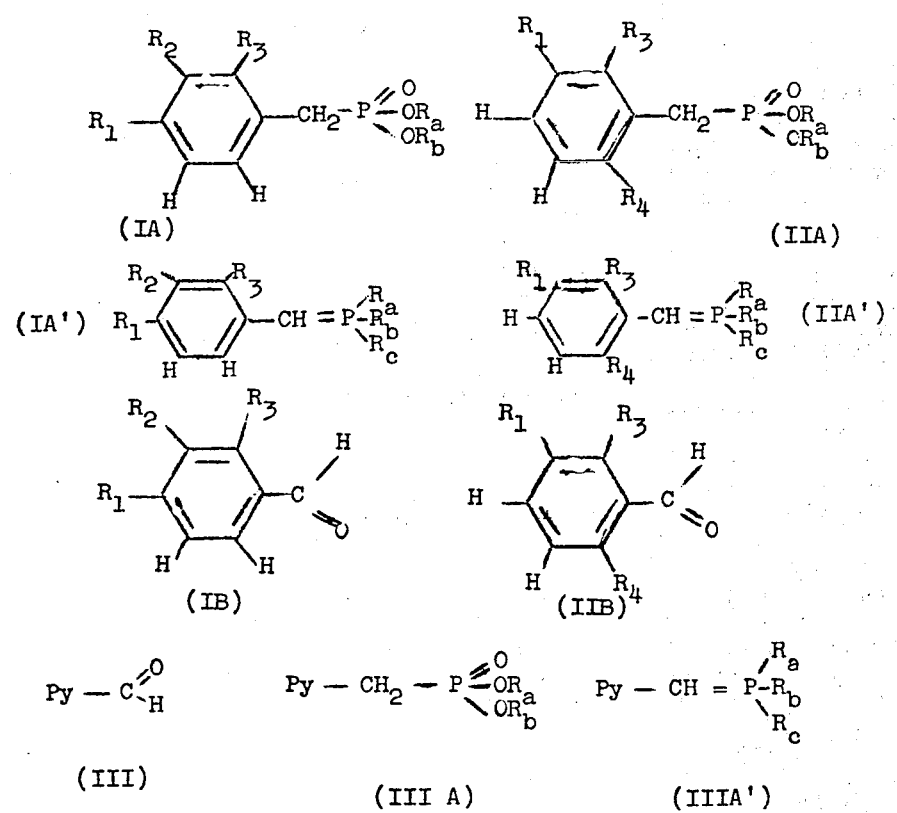

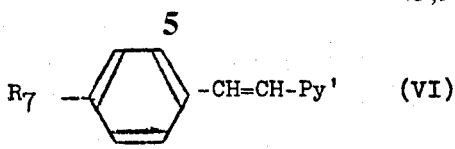 (VI)

wherein R$_7$ is as defined above with respect to formula (V), and Py' represents a 2- or 4- pyridyl group and the process comprises condensing a compound of formula (VII) with a compound of formula (VIII)

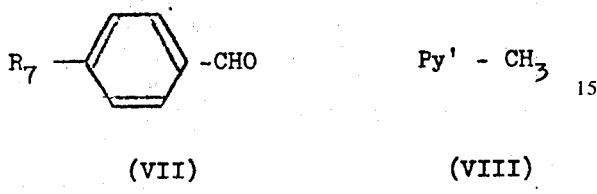

(VII)                    (VIII)

in the presence of a dehydrating agent.

Examples of suitable dehydrating agents include sulphuric acid, trifluoroacetic acid anhydride, and other carboxylic acid anhydrides, particularly acetic anhydride. The reaction is preferably carried out at an elevated temperature, for example in the range 50°–200°C.

The following alternate processes of the present invention permit the preparation of compounds of formula (XI):

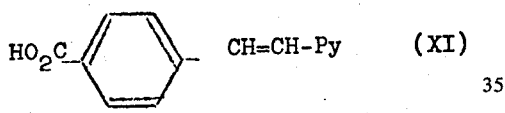 (XI)

or a salt thereof
wherein Py represents a 2-, 3-, or 4-pyridyl group:

a. Acid or base catalysed hydrolysis of a compound of formula (XII):

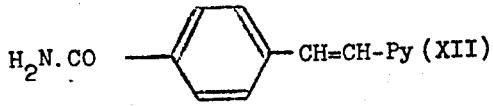 (XII)

wherein Py is as defined in formula (XI). Hydrolysis of amides may be carried out using a mineral acid as catalyst suitably hydrochloric acid or sulphuric acid. Base catalysed hydrolysis may be carried out using an alkali metal or alkaline earth metal hydroxide e.g. sodium or potassium hydroxide. Suitably the hydrolysis reaction is carried out in aqueous solution and fairly severe reaction conditions are preferred e.g. refluxing for several hours. The desired compound can be isolated as the free acid by neutralisation of the resultant reaction mixture or as the appropriate base addition salt (e.g. sodium salt if sodium hydroxide was employed)or acid addition salt (e.g. the hydrochloride if HCl was employed. Alternatively the free acid can be converted to any desired salt by standard procedures.

b. Acid or base catalysed hydrolysis of a compound of formula (XIII)

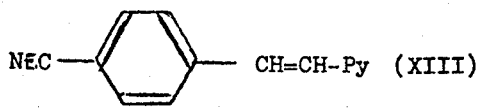 (XIII)

wherein Py is as defined in formula (XI) above. Ammonia is liberated during the hydrolysis of the nitrile compound (XIII) and thus the preferred catalyst is an acid which will bind the ammonia e.g. a hydrogen halide such as HCl or HBr. If base catalysed hydrolysis is used, ammonia is liberated and the acid will be obtained as an alkali salt or after neutralisation as the free acid.

c. Acid or base catalysed hydrolysis of a compound of formula (XIV)

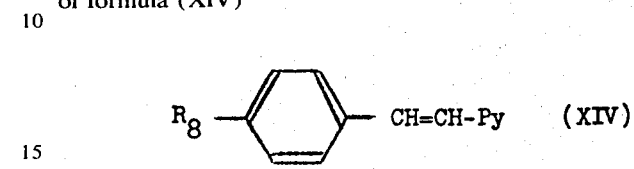 (XIV)

wherein R$_8$ is an esterified carboxylic acid group and Py is as defined in formula (XI). Preferably the process involves base hydrolysis using a strong base such as sodium hydroxide. The esterified carboxylic acid group R$_8$ may be for example a lower alkoxycarbonyl group such as methoxycarbonyl or tertiary butoxycarbonyl groups. The remarks made earlier about salts of the resultant free acid also apply in this case.

d. Reaction of a compound of formula (XV) with a hypohalite:

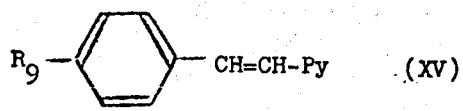 (XV)

wherein R$_9$ is an acyl group and Py is as defined in formula (XI). The acyl group R$_9$ may be an acetyl group (CH$_3$CO). Preferably the hypohalite reactant is sodium hypohalite which may be generated in situ in aqueous solution by the reaction of sodium hydroxide on a mixture of iodine and potassium iodide. Again the desired free acid may be isolated and converted to any desired salt by known methods.

e. Carbonation of a compound of formula (XVI) in an organic solvent followed by hydrolysis:

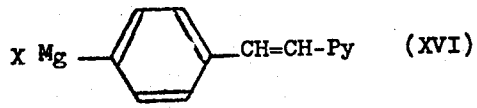 (XVI)

wherein Py is as defined in formula (XI) and X represents a halogen atom. Grignard reagents are of course well known in the art and the Grignard reagent (XVI) is prepared by known methods. The group X is preferably Br or Cl. Carbonation is preferably carried out using gaseous carbon dioxide but solid carbon dioxide may be used on occasions. Hydrolysis of the intermediate formed after carbonation can be carried out simply by the addition of water.

f. Oxidation of the formyl group of a compound of formula (XVII).

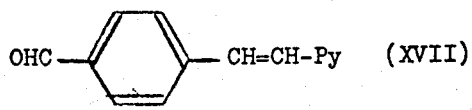 (XVII)

wherein Py is as defined in formula (XI). Suitable oxidising agents for the formyl group include silver oxide/-NaOH and concentrated nitric acid.

The following alternate processes of the present invention permit the preparation of compounds of formula (XVIII):

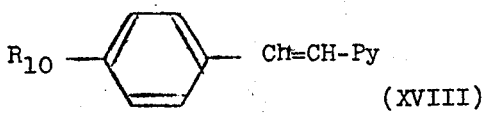

(XVIII)

wherein Py represents a 2-, 3-, or 4- pyridyl group; and $R_{10}$ represents an esterified carboxylic acid group.

a. Esterification of the corresponding compound wherein $R_{10}$ is a carboxylic acid grouup or the transesterification of a related compound wherein $R_{10}$ is a different esterified carboxylic acid group. Esterification is of course an extremely. well known reaction and standard procedures can be followed. Thus a compound of formula (XVIII) wherein $R_{10}$ is a carboxylic acid group can be reacted with an alcohol (e g ethanol) in the presence of an acid catalyst. Also a compound of formula (XVIII) wherein $R_{10}$ is an esterified carboxylic acid group (e g methoxycarbonyl group) can react with a lower alcohol (e g ethanol) in the presence of a catalyst such as sodium ethoxide to give the new ester by transesterification (ester interchange).

b. Hydrolysis of a compound of formula (XIX)

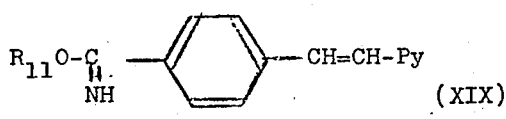

(XIX)

wherein Py is as defined in formula (XVIII) and $R_{11}$ is the hydrocarbon residue of an alcohol or phenol. Hydrolysis of the imino grouup HN=C< thus converting the group

into an esterified carboxylic acid group $R_{11}O.CO$-.

As previously indicated the compounds of this invention possess hypoglycemic activity. Thus in another of its aspects the present invention provides a pharmaceutical composition comprising a compound of formula (I) or (II) or a pharmaceutically acceptable salt thereof together with one or more pharmaceutically acceptable carriers.

As is common practise such compositions will usually be accompanied by or associated with written or printed directions for use in the medical treatment concerned in this case as an agent for the treatment of hyperglycemia, and may be formulated for oral or parenteral administration.

In forming the novel compositions of this invention the compound is incorporated in a suitable carrier such as for example a pharmaceutical carrier beverage or foodstuff. The compositions may take the form of tablets linguets, powders capsules slurries troches or lozenges. Any suitable pharmaceutical carrier may be used for formulating solid compositions such as for example, magnesium stearate starch lactose glucose sucrose rice flour, talc and chalk. The composition may also be in the form of an ingestible capsule (e g of gelatin) to contain the compound; or in the form of a syrup a liquid solution of a suspension. Suitable liquid pharmaceutical carriers include ethyl alcohol glycerine saline and water together with flavouring or colouring agents to form syrups.

A suitable dosage range for administration of the compounds of the invention is from 0.5 to 30 mg/kg/day preferably about 5 mg/kg/day. The following examples illustrate the preparation and properties of some of the compounds of the present invention.

EXAMPLE I 2-(4-Methoxycarbonylstyryl) pyridine

4-Toluic acid (20.40 g) methanol (200 ml) and concentrated sulphuric acid (10 ml) were refluxed 4 hours the solution cooled and the excess methanol removed under reduced pressure. The residue was poured into 500 ml cold water and the solution extracted three times with chloroform. The chloroform extracts were combined washed firstly with saturated aqueous sodium Bicarbonate and then with water dried over $MgSO_4$ the chloroform distilled off and the residue allowed to crystallise to give 21.52 g (96%) Methyl-4-toluate Methyl-4-toluate (21.52 g) N-bromo succinimide (25-70g) and α-azobutyronitrile (0.05 g) were refluxed in 400 ml carbon tetra-chloride until the reaction was complete. The succinimide was filtered off and the carbon tetrachloride distilled off to give 32.80 g (98%) Methyl-4-bromomethyl benzoate.

Methyl-4-bromomethyl benzoate (22.9 g) and triethylphosphite (16.00 g) were refluxed for 2½ hours. The excess triethylphosphate was distilled off and the residue added to 130 ml dimethylformamide containing dry sodium methoxide (prepared from 2.3 g sodium) at 5°C. 2-Pyridine carboxaldehyde (10.74 g) was added and the mixture stirred for 1 hour at room temperature. The mixture was heated at 80°C for 1 hour, cooled poured into 400 ml ice water and the solid filtered off and dried. The product was recrystallised from ethanol water (80/20). This gave 2.78 g (10.8%)2-(4-methoxycarbonylstyryl) pyridine MPT 120°C.

EXAMPLE 2

2-(4-Carboxy styryl)pyridine 2-(4-Methoxycarbonylstyryl) pyridine (2.00g) and 20% w/v aqueous sodium hydroxide (100 ml) were stirred and refluxed for 2 hours. The reaction mixture was cooled, acidified with glacial acetic acid the solid filtered off, dried and recrystallised from ethanol. This gave 1.68 g (90%) 2 Carboxy styryl) pyridine MPT 228°C.

EXAMPLE 3

The following table gives details of compounds prepared by methods analogous to the methods described in Examples 1 and 2. The table also gives details of the hypoglycemic activity of the compounds as measured in all examined mice. The hypoglycemic activity was scored by measuring the fall in blood sugar caused by a dose of 300 mg/kg of the compound administered intraperitoneally in carboxy methyl-cellulose.

Score Key:
0 = <5%
1 = 5–15%
2 = 15–25%
3 = 25–40%
4 =< 40%

| Name & Structure | Molecular formula | Molecular weight | ANALYSES C % expected % found % found | H | N | BPT MPT °C | Hypoglycemic activity |
|---|---|---|---|---|---|---|---|
| 2-(4-Methyl styryl)-pyridine | $C_{14}H_{13}N_1$ | 195 | 86.15 / 85.58 / 85.94 | 6.66 / 6.74 / 6.74 | 7.18 / 7.12 / 7.05 | MPT 168 | 3 |
| 3-(4-Methyl styryl)-pyridine | $C_{14}H_{13}N_1$ | 195 | 86.15 / 86.51 / 86.35 | 6.66 / 6.22 / 6.22 | 7.18 / 7.62 / 6.65 | MPT 166–8 | 3 |
| 4-(4-Methyl styryl)-pyridine | $C_{14}H_{13}N_1$ | 195 | 86.15 / 85.80 | 6.66 / 6.79 | 7.18 / 7.09 | MPT 154–5 | 3 |
| 2-(4-Carboxy styryl)-pyridine | $C_{14}H_{11}N_1O_2$ | 225 | 74.66 / 74.02 / 73.64 | 4.88 / 4.97 / 4.96 | 6.22 / 6.00 / 6.06 | MPT 228 | 3 |
| 3-(4-Carboxy styryl)-pyridine | $C_{14}H_{11}N_1O_2$ | 225 | 74.66 / 74.36 / 74.28 | 4.88 / 5.06 / 5.02 | 6.22 / 6.14 / 6.07 | MPT 270–5 | 3 |
| 4-(4-Carboxy styryl)-pyridine[1] | $C_{14}H_{11}N_1O_2$ | 225 | 74.66 / 73.66 / 73.67 | 4.88 / 4.97 / 4.98 | 6.22 / 6.14 / 5.98 | MPT >300 | 3 |

-continued

| Name & Structure | Molecular formula | Molecular weight | ANALYSES % expected % found % found | C | H | N | BPT MPT °C | Hypoglycemic activity |
|---|---|---|---|---|---|---|---|---|
| 2-(4-Methoxycarbonyl styryl)-pyridine | $C_{15}H_{13}N_1O_2$ | 225 | | 75.31<br>74.98<br>75.08 | 5.44<br>5.54<br>5.64 | 5.86<br>5.38<br>5.55 | MPT 120 | 2 |

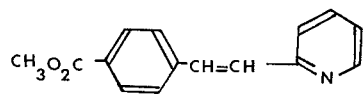

| 3-(4-methoxycarbonyl styryl)- | $C_{15}H_{13}N_1O_2$ | 239 | | 75.31<br>75.96<br>75.28 | 5.44<br>5.43<br>5.40 | 5.86<br>5.46<br>5.61 | MPT 116 | 2 |

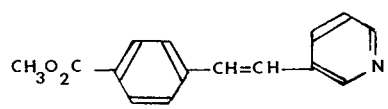

(1)Could not be purified by recrystallisation.

| 4-(4-Methoxycarbonyl styryl)-pyridine | $C_{15}H_{13}N_1O_2$ | 239 | | 75.31<br>74.91<br>74.55 | 5.44<br>5.35<br>5.39 | 5.86<br>5.23<br>5.01 | MPT 118 | 2 |

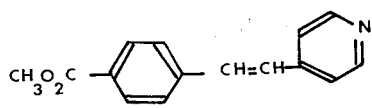

| 2-(4-Ethoxycarbonyl styryl)-pyridine | $C_{16}H_{15}N_1O_2$ | 253 | | 75.88<br>75.45<br>75.54 | 5.92<br>5.86<br>5.99 | 5.53<br>5.42<br>5.50 | MPT 108-9 | 4 |

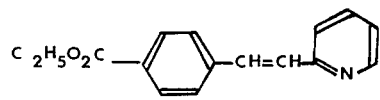

| 3-(4-Ethoxycarbonyl styryl)-pyridine | $C_{16}H_{15}N_1O_2$ | 253 | | 75.88<br>75.52<br>75.54 | 5.92<br>6.09<br>6.03 | 5.53<br>5.51<br>5.50 | MPT 98 | 3 |

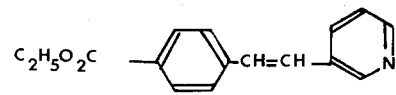

| 4-(4-Ethoxycarbonyl Styryl)-pyridine | $C_{16}H_{15}N_1O_2$ | 253 | | 75.88<br>75.00<br>75.11 | 5.92<br>6.05<br>5.97 | 5.53<br>5.38<br>5.34 | MPT 83 | 3 |

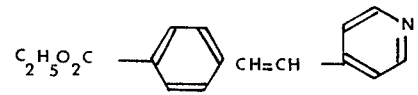

Examples 4–9 illustrates alternative methods of preparation for the compounds of this invention.

EXAMPLE 4

PREPARATION OF 3(4-ETHOXYCARBONYL STYRYL) PYRIDINE

To 3(4-cyanostyryl) pyridine (0.5 g) was added 95% ethanol (20ml) and conc. $H_2SO_4$ (1 ml). The reaction was then heated at 120°C for 22 hrs. The reaction mixture was cooled, diluted with water and basified using sodium bicarbonate. The product was extracted with ether. Mpt 98°C.

EXAMPLE 5

PREPARATION OF 3(4-CARBOXY STYRYL) PYRIDINE

3(4-cyanostyryl) pyridine (0.5 g) and 48% HBr (20 ml) refluxed together for 4 hrs. The reaction was cooled and the acid hydrobromide that crystallised was filtered off. Mpt over 300°C.

EXAMPLE 6

ESTERIFICATION OF 3(4-CARBOXY STYRYL) PYRIDINE

3(4-Carboxystyryl) pyridine (0.5 g) was refluxed with ethanol (50 ml) and conc. $H_2SO_4$ (0.5 ml) for 2 hrs. The ethanol was removed and the ester extracted with ethyl acetate neutralising any acid with sodium bicarbonate. Recrystallised from pet. ether 60/80 . Mpt 98°C.

EXAMPLE 7

PREPARATION OF 3(4-METHYL STYRYL) PYRIDINE p-Tolualdehyde (12.0 g), 3-picoline (8.6 g) and acetic anhydride (10.2 g) were heated at 160°C for 16 hrs. The reaction mixture was then poured hot into 10% NaOH (60 ml). The solid which crystallised was filtered off and subjected to column chromatography with neutral alumina using chloroform as solvent. Mpt. 166°C.

EXAMPLE 8

PREPARATION OF 3(4-BENZOYL STYRYL) PYRIDINE a. PREPARATION OF 3(4-CYANOSTYRYL) PYRIDINE

4-Cyanobenzyl bromide (18.2 g) and triethyl phosphite (24 g) were refluxed for 2½ hrs. The excess triethylphosphite was distilled off. The residue was then added dropwise into a solution of sodium methoxide (5.4 g dissolved in DMF (150 ml) at 0°C. 3-pyridyl carboxaldehyde (10.7 g) was then added and the reaction heated for 4 hours. The reaction mixture was poured hot in crushed ice and the product filtered off. It was recrystallised from ethanol water. Mpt 128°C.

b. REACTION OF 3(4-CYANOSTYRYL) PYRIDINE AND PHENYL MAGNESIUM BROMIDE

Phenyl magnesium bromide was prepared in the usual manner using magnesium turnings (0.96 g) and bromobenzene (6.28 g) in dry ether (120 ml) (4 times excess Grignard reagent used). To the phenyl magnesium bromide was added 3(4-cyanostyryl) pyridine (2 g) as a suspension in ether. The reaction was refluxed 4 hrs then poured onto crushed ice. The product was extracted in ether and recrystallised from ethanol/petrol 60/80. Mpt 106°C.

EXAMPLE 9

PREPARATION OF 2(4-HYDROXYMETHYLSTYRYL) PYRIDINE

Sodium dihydro bis (2-methoxyethoxy) aluminate (7.25 g. 0.025 m) was added dropwise to a solution of 2-(4-ethoxycarbonylstyryl) pyridine (6.35 g 0.25 m) in 100 ml dry ether. The mixture was stirred for 3 hours at room temperature followed by gently refluxing for a further 3 hours. On cooling, 20% sodium hydroxide solution was added to the reaction mixture. The ether layer was separated and dried over anhydrous magnesium sulphate. The solvent was removed by rotary evaporation and the solid which was removed was recrystallised from ethanol. The product was identified and shown to be pure by G.L.C. I.R. N.M.R. and analysis.

EXAMPLE 10

The following table gives the activity of further compounds measured by the method described in Example 3 and using the same score key.

| NAME AND STRUCTURE | Hypoglycemic Activity |
|---|---|
| 2-(2 5-dimethylstyryl)-pyridine 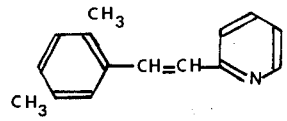 | 2 |
| Prepared by the method of Example 1 2-(3 4-dimethylstyryl)-pyridine 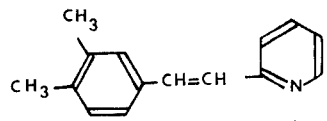 | 1 |

-continued

| NAME AND STRUCTURE | Hypoglycemic Activity |
|---|---|
| Prepared by the method of Example 1<br>2-(4-hydroxymethylstyryl)-pyridine<br>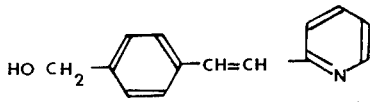 | 3 |
| Preparation: see Example 9<br>3-(4-benzoylstyryl)-pyridine<br>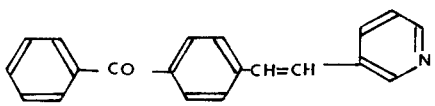 | 1 |
| Preparation: see Example 8 | |

We claim:

1. The compound 2-(4-ethoxycarbonylstyryl)-pyridine of formula:

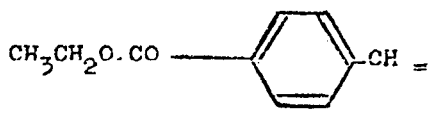

2. A pharmaceutical composition useful for the treatment of hyperglycemia comprising an effective dose of an antihyperglycemic compound together with one or more pharmaceutically acceptable carriers, said compound being 2-(4-ethoxycarbonylstyryl)-pyridine.

3. A method for the treatment of hyperglycemia in human beings which method comprises administering to the hyperglycemic patient an effective dose of 2-(4-ethoxycarbonylstyryl) pyridine or a pharmaceutically acceptable salt thereof.

* * * * *